(12) United States Patent
Miller et al.

(10) Patent No.: US 6,589,980 B2
(45) Date of Patent: Jul. 8, 2003

(54) SUBSTITUTED 10,11-BENZO[B]FLUOREN-10-ONES AS ESTROGENIC AGENTS

(75) Inventors: Christopher P. Miller, Wayne, PA (US); Michael D. Collini, Clifton Heights, PA (US); Heather A. Harris, Phoenixville, PA (US); James C. Keith, Jr., Andover, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/146,562

(22) Filed: May 15, 2002

(65) Prior Publication Data

US 2003/0087955 A1 May 8, 2003

Related U.S. Application Data

(60) Provisional application No. 60/291,509, filed on May 17, 2001.

(51) Int. Cl.[7] ...................... A61K 31/35; C07D 311/78
(52) U.S. Cl. ........................................ 514/453; 549/383
(58) Field of Search ............................ 514/453; 549/383

(56) References Cited

U.S. PATENT DOCUMENTS

| | | |
|---|---|---|
| 5,424,331 A | 6/1995 | Shlyankevich |
| 5,516,528 A | 5/1996 | Hughes et al. |
| 5,523,087 A | 6/1996 | Shlyankevich |
| 5,952,374 A | 9/1999 | Clarkson, Jr. et al. |

FOREIGN PATENT DOCUMENTS

| | | |
|---|---|---|
| DE | 195 24 937 | 1/1997 |
| DE | 196 54 750 | 7/1998 |
| EP | 0 993 781 | 4/2000 |
| EP | 1 060 744 | 12/2000 |
| WO | WO 98/03180 | 1/1998 |
| WO | WO 98/21946 | 5/1998 |
| WO | WO 98/26784 | 6/1998 |
| WO | WO 98/29129 | 7/1998 |
| WO | WO 99/17767 | 4/1999 |
| WO | WO 00/30663 | 6/2000 |
| WO | WO 00/30664 | 6/2000 |

OTHER PUBLICATIONS

Yasuyuki Hashidoko et al., Agric. Biol. Chem., 1986, 1797–807, 50.
Naoki Abe et al., Agric. Biol. Chem., 1987, 349–53, 51.
Song S. Yang et al., Phytochemistry, 1989, 1749–50, 28.
Fujinori Hanawa et al., Phytochemistry, 1991, 157–63, 30.
Fujinori Hanawa et al., Heterocycles, 1991, 1563–70, 32.
Hubert Gagnon et al., J. Chromatogr., 1992, 255–9, 606.
Ushio Sankawa et al., Curr. Plant Sci. Biotechnol. Agric., 1995, 595–604, 22.
Przemyslaw Wojtaszek et al., Plant Physiol. Biochem., 1997, 129–135, 35.
O. Mellenthin et al., J. Agric. Food Chem., 1999, 594–602, 47.
H.A. Hassanean, Bull. Pharm. Sci., Assiut. Univ., 1998, 109–115, 21.
Mitsuyoshi Sakasai et al., J. Biosci., 2000, 165–174, 55.
John J.B. Anderson et al., C. Nutr. Res. Rev., 1999, 75–116, 12.
Satoshi Tahara et al., Agric. Biol. Chem., 1985, 1775–83, 49.

*Primary Examiner*—Amelia Owens
(74) *Attorney, Agent, or Firm*—Arnold S. Milowsky

(57) ABSTRACT

This invention provides estrogen receptor modulators of formula I, having the structure

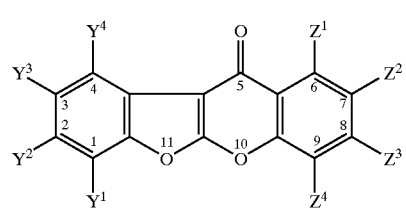

wherein
  $X$, $Y^1$, $Y^2$, $Y^3$, $Y^4$, $Z^1$, $Z^2$, $Z^3$, and $Z^4$ are as defined in the specification, or a pharmaceutically acceptable salt thereof.

15 Claims, No Drawings

SUBSTITUTED 10,11-BENZO[B]FLUOREN-10-ONES AS ESTROGENIC AGENTS

This application claims priority from provisional application Serial No. 60/291,509, filed May 17, 2001, the entire disclosure of which is hereby incorporated by reference.

BACKGROUND OF THE INVENTION

This invention relates to 10,11-benzo[b]fluoren-10-ones which are useful as estrogenic agents.

The pleiotropic effects of estrogens in mammalian tissues have been well documented. (Dey, M.; Lyttle, C. R.; Pickar, J. H. Maturitas (2000), 34(S2), S25–S33. Speroff, L Ann. N. Y. Acad. Sci. (2000), 900, 26–39. Nozaki, M. Ernst Schering Res. Found. Workshop (2000), Suppl. 4, 115–125). The estrogen receptor (ER), a member of the nuclear hormone receptor family, regulates transcription through its interactions with a large number of proteins including co-activators and co-repressors (collectively referred to as coregulators) and an estrogen response element (ERE). In addition to its ability to effect the cellular transcription machinery through the ERE, ER can also affect transcriptional processes independent of its direct interaction with DNA. For example, it has been demonstrated that 17β-estradiol can inhibit IL-6 promoter activity. This inhibition requires 17β-estradiol binding to the receptor, but does not depend on having a functional DNA-binding domain (Ray, A.; Prefontaine, K. E.; Ray, P. J. J Biol. Chem., 1994, 269, 12940). Even the unliganded receptor may affect the transcription process after phosphorylation of serine residues, especially in the AF-1 containing AB domains of the receptor.

Recently, a second ER receptor (ERβ) with high affinity for 17β-estradiol has been identified. A comparison of the physical structure of ERβ with the first to be identified estrogen receptor (ERα) reveals that ERβ is shorter in length (530 AA vs. 595 AA) but contains the same functional domains although the AB domains of ERβ are somewhat truncated relative to ERα (148AA vs. 180AA) and not surprisingly, the AF-1 activation potential between the two receptors is different (McInerney, Eileen M.; Weis, Karen E.; Sun, Jun; Mosselman, Sietse; Katzenellenbogen, Benita S. Endocrinology (1998), 139(11), 45134522). The C domain (DNA-binding domain) displays remarkable homology between the two receptors (96%) and a fortiori, the two receptors would be expected to bind with similar affinities to a given ERE. However, although it has been shown that the two receptors bind to ERE's vitogenellin, c-fos, c-jun, pS2, cathepsin D, and acetylcholine transferase, they do not necessarily bind with the same affinity (Hyder, S. M., Chiappetta, C., Stancel, G. M. Biochem. Pharmacol. (1999), 57, 597–601). In contrast, the E domain (ligand binding domain or LBD) of the two receptors share only a 60% homology. However, structural analyses of the two receptors indicates that the residues in the ligand contact area are very similar, with only two residues different (ERα 421(Met) ERβ 373(Ile); ERα 384 (Leu) ERβ 336(Met)). Additionally, the variations in the overall sequence of the two receptors may also lead to different interactions between the subtypes and the various coregulatory proteins that enable or modify the ER transcriptional machinery. In fact, preliminary studies suggest that the coregulator SRC-3 interacts to a much greater extent with ERα than with ERβ (Suen, Chen-Shian; Berrodin, Thomas J.; Mastroeni, Robert; Cheskis, Boris J.; Lyttle, C. Richard; Frail, Donald J. Biol. Chem. (1998), 273(42), 27645–27653).

Besides the differential interaction of the two receptors with various coregulatory proteins, the two receptors also have tissue distribution that is not coextensive. Even within a given tissue where both receptors are coexpressed there is sometimes localization of one of the receptors in a given cell-type. For example, in the human ovary, both ERα and ERβ RNA expression can be detected. Immunostaining demonstrates that ERβ is present in multiple cell types including granulosa cells in small, medium and large follicles, theca and corpora lutea, whereas ERα was weakly expressed in the nuclei of granulosa cells, but not in the theca nor in the corpora lutea (Taylor, A. H.; Al-Azzawi, F. J. Mol. Endocrinol. (2000), 24(1), 145–155). In the endometrium, immunostaining showed both ERα and ERβ in luminal epithelial cells and in the nuclei of stromal cells but, significantly, ERβ appears to be weak or absent from endometrial glandular epithelia (Taylor, et al). Epithelial cells in most male tissues including the prostate, the urothelium and muscle layers of the bladder, and Sertoli cells in the testis, are also immunopositive for ERβ. Significant ERβ immunoreactivity has been detected in most areas of the brain, with the exception of the hippocampus, a tissue that stained positive for only ERα, ibid.

Estrogens have been shown to exert a positive effect on the cardiovascular system that may help to explain the increased risk of cardiovascular disease observed in the post-menopause period. While some of the cardiovascular benefit may occur through estrogen action on the liver via upregulation of the LDL receptor (thus decreasing LDL levels, presumably an ERα mediated response), it is also likely that direct action on the arterial wall also has a role. It has been demonstrated that after a vascular injury event (denudation of rat artery), ERβ message in the endothelial cells is upregulated by as much as 40 times that of ERα (Makela, Sari; Savolainen, Hanna; Aavik, Einari; Myllarniemi, Marjukka; Strauss, Leena; Taskinen, Eero; Gustafsson, Jan-Ake; Hayry, Pekka. (1999), 96(12), 7077–7082). In addition, 17β-estradiol was able to inhibit the vascular injury response in an ERα knockout mouse, although this same response was also inhibited in an ERβ knockout mouse (Iafrati, Mark D.; Karas, Richard H.; Aronovitz, Mark; Kim, Sung; Sullivan, Theodore R., Jr.; Lubahn, Dennis B.; O'Donnell, Thomas F., Jr.; Korach, Kenneth S.; Mendelsohn, Michael E. Nat. Med. (N.Y.) (1997), 3(5), 545–548. Karas, Richard H.; Hodgin, Jeffrey B.; Kwoun, Moon; Krege, John H.; Aronovitz, Mark; Mackey, William; Gustafsson, Jan Ake; Korach, Kenneth S.; Smithies, Oliver; Mendelsohn, Michael E. Proc. Nat. Acad. Sci. U. S. A. (1999), 96(26), 15133–15136). Provided that the response is not being inhibited by a yet unidentified estrogen receptor, it is likely that the injury response could be inhibited by ligands that are selective for either one of the two receptors.

When the typical estrogen binds with an ER receptor, the receptor dissociates from HSP 90 as well as other molecular chaperones, and dimerizes with another receptor. Since this mechanism of activation is shared by both ER receptors, the possibility exists for heterodimerization to take place in tissues where both receptors are expressed. Indeed, heterodimers of ERα and ERβ bind DNA with an affinity equal to that of ERα homodimers and greater than ERβ homodimers (Cowley, Shaun M.; Hoare, Susan; Mosselman, Sietse; Parker, Malcolm G. J. Biol. Chem. (1997), 272(32), 19858–19862).

DESCRIPTION OF THE INVENTION

This invention provides estrogenic compounds of formula I, having the structure

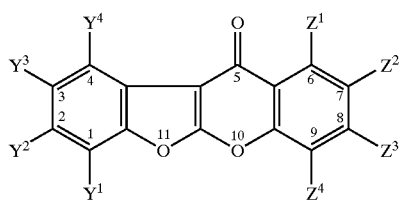

wherein $Y^1, Y^2, Y^3, Y^4, Z^1, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO$_2$, or —$COR^3$;

R is hydrogen, alkyl of 1–6 carbon atoms, —$CF_3$, benzyl, —$CO_2R^1$, or —$COR^3$;

$R^1$ is —$CF_3$, alkyl of 1–6 carbon atoms, or benzyl;

$R^2$ is hydrogen or alkyl of 1–6 carbon atoms;

$R^3$ is alkyl of 1–6 carbon atoms, phenyl, thienyl, furyl, —$NR^4R^5$, or —$CF_3$;

$R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1, Y^2, Y^3, Y^4, Z^1, Z^2, Z^3$, and $Z^4$ is —OR.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The term alkyl includes both branched and straight chain moieties. By definition alkyl also includes alkyl moieties which are optionally mono- or poly substituted with groups such as halogen, hydroxy, cyano, alkoxy, aryloxy, arylalkyl, alkylthio, arylthio, amino, alkylamino, and dialkylamino. The term halogen includes bromine, chlorine, fluorine, and iodine.

As used in accordance with this invention, the term "providing," with respect to providing a compound or substance covered by this invention, means either directly administering such a compound or substance, or administering a prodrug, derivative, or analog which will form the effective amount of the compound or substance within the body.

Of the compounds of this invention, it is preferred that $Y^1, Y^2, Y^3, Y^4, Z^1, Z^2, Z^3$, and $Z^4$ are hydrogen, or —OR; it is more preferred that that R is hydrogen or alkyl of 1–6 carbon atoms.

The reagents used in the preparation of the compounds of this invention can be either commercially obtained or can be prepared by standard procedures described in the literature.

The compounds of this invention can be very efficiently prepared by the routes indicated in the synthetic schemes shown below. Scheme I shows the preparation of lupinalbin A (4). The starting material for the synthesis was the commercially available 2,4-dimethoxyphenylacetic acid 5 (Aldrich Chemical) which was first converted to the acid chloride by treatment with $SOCl_2$ and then reacted with 1,3,5-trimethoxybenzene in the presence of $AlCl_3$ to render the desoxybenzoin 6. The desoxybenzoin was selectively demethylated by $AlCl_3$ to yield compound 7. The desoxybenzoin 7 was subsequently reacted with triethylorthoformate and morpholine to render the tetramethoxy isoflavone 8. Completely demethylating 8 proved to be a little difficult and it was found that the compound could be cleanly tridemethylated by treatment with $BBr_3$ in $CH_2Cl_2$ to render compound 9. The trisphenolic compound was then oxidatively cyclized by heating the precursor 9 with DDQ in THF at reflux. The 7-methylether analogue of lupinalbin A 10 was then converted to lupinalbin A 4 by heating in neat Pyr-HCl.

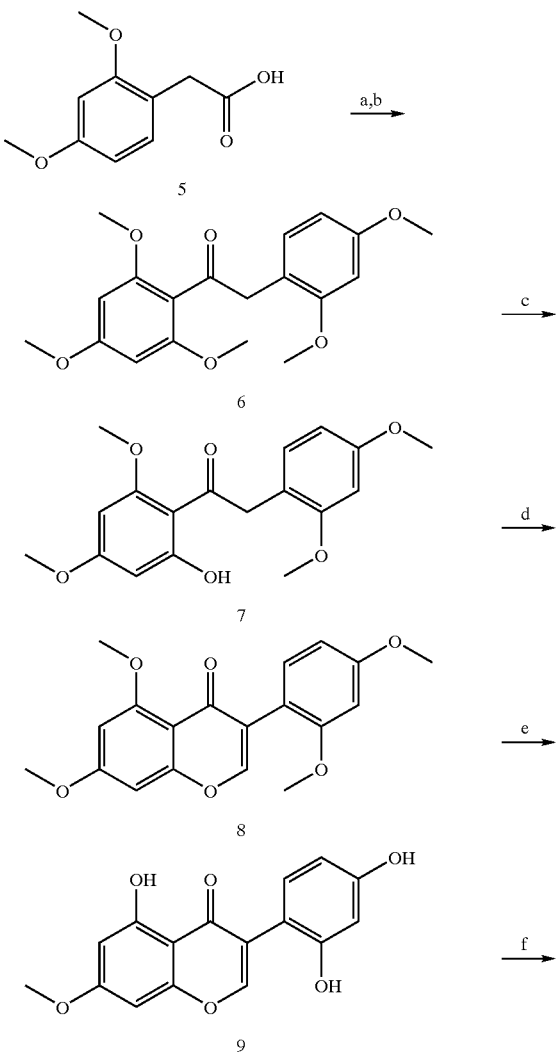

Scheme 1

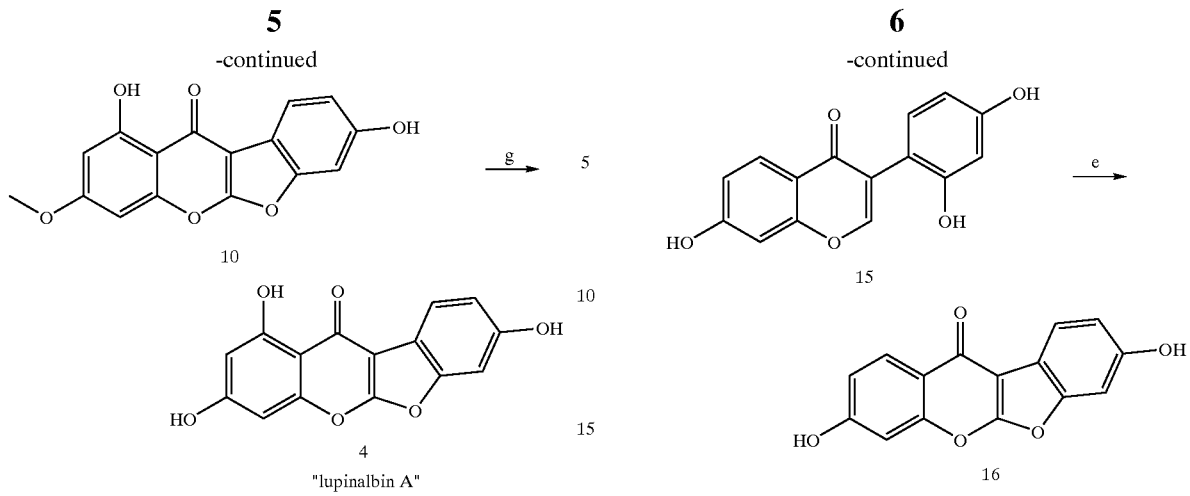

<sup>a</sup>Reagents and conditions: (a) SOCl₂, THF; (b) 1,3,5-trimethoxybenzene, 1,2-dichloroethane; (c) AlCl₃, CHCl₃; (d) CH(OEt)₃ morpholine (e) BBr₃, CH₂Cl₂; (f) THF, DDQ; (g) Pyr-HCl, heat <sup>a</sup>Reagents and conditions: (a) DMF (di-ethyl acetyl), Tol; (b) Br₂, CH₂Cl₂ (c) 2,4-dimethoxy benzene boronic acid, Pd(Ph₃)₄, Tol/EtOH, Na₂CO₃ (d) BBr₃, CH₂Cl₂; (f) Dioxane, DDQ An alternative preparation of compounds of this invention is illustrated in scheme 2 for the preparation of analog 16. This route utilizes the 3-bromo chromenone 13 as a precursor for the Suzuki coupling reaction that renders isoflavone 14. Isoflavone is then taken to the final product in a similar fashion as explained in Scheme 1. In this case, however, complete demethylation to 15 occurred under the BBr₃ ether cleavage conditions.

In addition to compound 16 (scheme 2), lupinalbin A 4 (scheme 1) and its novel precursor 10 (scheme 1), other novel analogues are claimed where alternatively substituted starting materials result in final products wherein $Y^{1-4}$ and $Z^{1-4}$ are incorporated onto the tetracycle ring structure. For example, as can be seen in Scheme 3, simply starting with variously substituted phenylacetic acids 17 as well as the appropriately substituted methoxybenzenes 18 gives the intermediate 19, which can be taken onto the final products 20 in analogous fashion to that already shown. Alternatively, as shown in scheme 2, the Suzuki mediated coupling of various 3-halo chromenones with various boronic acids renders additional analogues of the claimed genus.

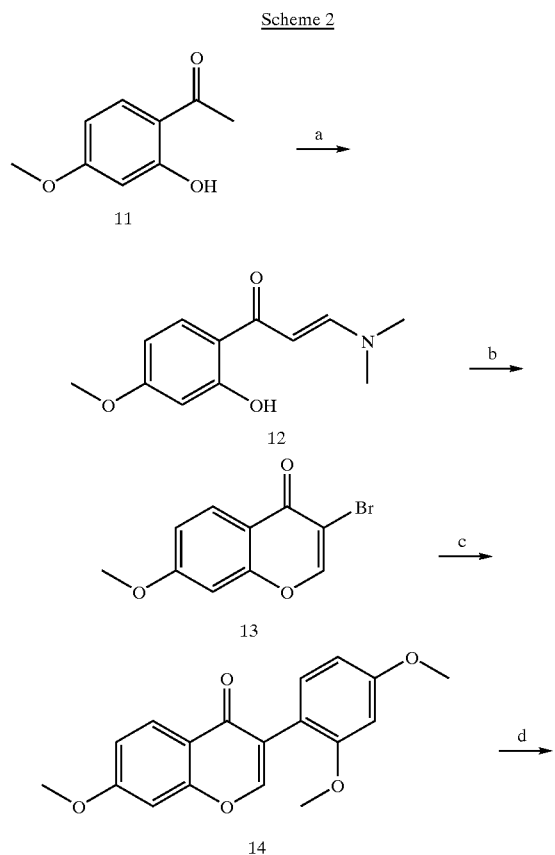

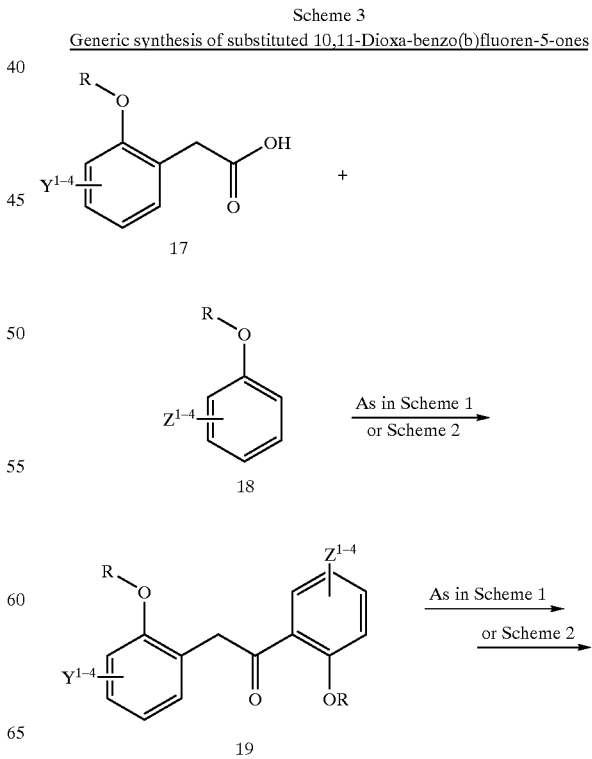

Scheme 3
Generic synthesis of substituted 10,11-Dioxa-benzo(b)fluoren-5-ones

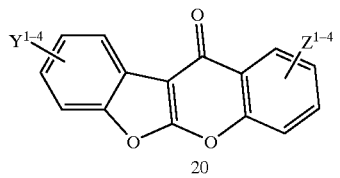

Representative examples of the invention were evaluated for their ability to compete with 17β-estradiol for both ERα and ERβ. This test procedure provides the methodology for one to determine whether a particular compound binds to the estrogen receptor (and is therefore "estrogenic") and whether there is selectivity for ERα or ERβ. The values are shown in the Table infra and are reported as $IC_{50}$s. 17β-estradiol is included as a standard reference for comparison. The procedure used is briefly described below. A crude lysate of E. coli expressing the estrogen receptor ligand binding domains (D,E, & F) of human ERα or ERβ was prepared. Both receptors and compounds were diluted in 1×Dulbecco's PBS (DPBS) supplemented with 1 mM EDTA. Using a high binding masked microtiter plate, 100 uL of receptor (1 uG/well) was combined with 2 nM [$^3$H]-17β-estradiol and various concentrations of compound. After between 5 and 15 hours at room temperature, the plates were washed with DPBS/1 mM EDTA and bound radioactivity determined by liquid scintillation counting. The $IC_{50}$ is defined as the concentration of compound that decreases total 17β-estradiol binding by 50%. The results obtained are described in the table below.

TABLE

ER-binding affinities for representative examples of invention

| Compound | ERβ $IC_{50}$ (uM) | ERα $IC_{50}$ (uM) |
|---|---|---|
| 17β-estradiol | 0.004 | 0.003 |
| 4 Lupinalbin A | 0.002 | 0.028 |
| 10 | 0.127 | 2.73 |
| 16 | 0.028 | 0.482 |

The results obtained in the standard pharmacologic test procedure demonstrate that the compounds of this invention are estrogenic compounds, some with preferential affinity for the ERβ receptor, but still are considered active at the ERα receptor. Thus, compounds of this invention will span a range of activity based, at least partially, on their receptor affinity selectivity profiles. Additionally, since each novel receptor ligand complex is unique and thus its interaction with various coregulatory proteins is unique, compounds of this invention will display different modulatory behavior depending on the cellular context they are in. For example, in some cell-types, it is possible for a compound to behave as an estrogen agonist while in other tissues, an antagonist. Compounds with such activity have sometimes been referred to as SERMs (Selective Estrogen Receptor Modulators). Unlike many estrogens, however, many of the SERMs do not cause increases in uterine wet weight. These compounds are antiestrogenic in the uterus and can completely antagonize the trophic effects of estrogen agonists in uterine tissue. These compounds, however, act as estrogen agonists in the bone, cardiovascular, and central nervous systems. Due to this tissue selective nature of these compounds, they are useful in treating or preventing in a mammal disease states or syndromes which are caused or associated with an estrogen deficiency (in certain tissues such as bone or cardiovascular) or an excess of estrogen (in the uterus or mammary glands).

Even beyond such cell-specific modulation, compounds of this invention also have the potential to behave as agonists on one receptor type while behaving as antagonists on the other. For example, it has been demonstrated that compounds can be an antagonist on ERβ while being an agonist on ERα (Meyers, Marvin J.; Sun, Jun; Carlson, Kathryn E.; Katzenellenbogen, Benita S.; Katzenellenbogen, John A. J. Med. Chem. (1999), 42(13), 2456–2468). Such ERSM (Estrogen Receptor Selective Agonist Antagonist) activity provides for pharmacologically distinct estrogenic activity within this series of compounds.

Standard pharmacological test procedures are readily available to determine the activity profile of a given test compound. The following briefly summarizes several representative test procedures procedures. Standard pharmacological test procedures for SERMs are also provided in U.S. Pat. Nos. 4,418,068 and 5,998,402 which are hereby incorporated by reference.

Rat Uterotrophic/Antiuterotrophic Test Procedure

The estrogenic and antiestrogenic properties of the compounds can be determined in an immature rat uterotrophic assay (4 day) that (as described previously by L. J. Black and R. L. Goode, Life Sciences, 26, 1453 (1980)). Immature Sprague-Dawley rats (female, 18 days old) were tested in groups of six. The animals are treated by daily ip injection with 10 uG compound, 100 uG compound, (100 uG compound+1 uG 17β-estradiol) to check antiestrogenicity, and 1 uG 17β-estradiol, with 50% DMSO/50% saline as the injection vehicle. On day 4 the animals are sacrificed by $CO_2$ asphyxiation and their uteri removed and stripped of excess lipid, any fluid removed and the wet weight determined. A small section of one horn is submitted for histology and the remainder used to isolate total RNA in order to evaluate complement component 3 gene expression.

6-Week Ovariectomized Rat Test Procedure—Bone and Cardioprotection

Female Sprague Dawley CD rats, ovx or sham ovx, are obtained 1 day after surgery from Taconic Farm (weight range 240–275 g). They are housed 3 or 4 rats/cage in a room on a 12/12 (light/dark) schedule and provided with food (Purina 5K96C rat chow) and water ad libitum. Treatment for all studies begin 1 day after the animals arrival and dosed 7 days per week as indicated for 6 weeks. A group of age matched sham operated rats not receiving any treatment serve as an intact, estrogen replete control group for each study.

All treatments are prepared in 1% tween 80 in normal saline at defined concentrations so that the treatment volume is 0.0 mL/100 g body weight. 17β-estradiol is dissolved in corn oil (20 μg/mL) and delivered subcutaneously, 0.1 mL/rat. All dosages are adjusted at three week intervals according to group mean body weight measurements.

Five weeks after the initiation of treatment and one week prior to the termination of the study, each rat is evaluated for bone mineral density (BMD). The total and trabecular density of the proximal tibia are evaluated in anesthetized rats using an XCT-960M (pQCT; Stratec Medizintechnik, Pforzheim, Germany). The measurements are performed as follows: Fifteen minutes prior to scanning, each rat is anesthetized with an intraperitoneal injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 900 angle and the knee joint at 180°. The polycarbonate tube is affixed to a sliding platform that maintains it perpendicular to the aperture of the pQCT. The platform is adjusted so that the distal end of the femur and the proximal end of the tibia would be in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is automatically removed using an iterative algorithm. The density of the remaining bone (total density) is reported in $mg/cm^3$. The outer 55% of the bone. is peeled away in a concentric spiral. The density of the remaining bone (Trabecular density) is reported in $mg/cm^3$. One week after BMD evaluation the rats are euthanized by carbon dioxide suffocation and blood collected for cholesterol determination. The uteri are removed and the weights taken. Total cholesterol is determined using a Boehringer-Mannheim Hitachi 911 clinical analyzer using the Cholesterol/HP kit. Statitstics were compared using one-way analysis of variance with Dunnet's test.

MCF-7/ERE Antiproliferative Test Procedure

Stock solutions of test compounds (usually 0.1 M) are prepared in DMSO and then diluted 10 to 100-fold with DMSO to make working solutions of 1 or 10 mM. The DMSO stocks are stored at either 4° C. (0.1 M) or –20° C. (<0.1M). MCF-7 cells are passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000/well into 96 well plates and incubated at 37° C. overnight.

The cells are infected for 2 hr at 37° C. with 50 μl/well of a 1:10 dilution of adenovirus 5-ERE-tk-luciferase in experimental medium [phenol red-free D-MEM/F-12 medium containing 10% (v/v) heat-inactived charcoal-stripped fetal bovine serum, 1% (v/v) Penicillin-Streptomycin, 2 mM glutaMax-1, 1 mM sodium pyruvate]. The wells are then washed once with 150 μl of experimental medium. Finally, the cells are treated for 24 hr at 37° C. in replicates of 8 wells/treatment with 150 μl/well of vehicle (≦0.1% v/v DMSO) or compound that is diluted ≧1000-fold into experimental medium.

Initial screening of test compounds is done at a single dose of 1 μM that is tested alone (agonist mode) or in combination with 0.1 nM 17β-estradiol ($EC_{80}$; antagonist mode). Each 96 well plate also includes a vehicle control group (0.1% v/v DMSO) and an agonist control group (either 0.1 or 1 nM 17β-estradiol). Dose-response experiments are performed in either the agonist and/or antagonist modes on active compounds in log increases from $10^{-14}$ to $10^{-5}$ M. From these dose-response curves, $EC_{50}$ and $IC_{50}$ values, respectively, are generated. The final well in each treatment group contains 5 μl of $3×10^{-5}$ M ICI-182,780 ($10^{-6}$ M final concentration) as an ER antagonist control.

After treatment, the cells are lysed on a shaker for 15 min with 25 μl/well of 1×cell culture lysis reagent (Promega Corporation). The cell lysates (20 μl) are transferred to a 96 well luminometer plate, and luciferase activity is measured in a MicroLumat LB 96 P luminometer (EG & G Berthold) using 100 μl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS Institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the agonist mode, or the positive agonist control results (0.1 nM 17β-estradiol) in the antagonist mode. For the initial single dose experiment, if the compound treatment results are significantly different from the appropriate control (p<0.05), then the results are reported as the percent relative to the 17β-estradiol control [i.e., ((compound–vehicle control)/(17β-estradiol control–vehicle control))×100]. The JMP software is also used to determine the $EC_{50}$ and/or $IC_{50}$ values from the non-linear dose-response curves.

Inhibition of LDL Oxidation—Antioxidant Activity

Porcine aortas are obtained from an abattoir, washed, transported in chilled PBS, and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15–20 minutes, after which the collagenase solution is collected and centrifuged for 5 minutes at 2000×g. Each pellet is suspended in 7 mL of endothelial cell culture medium consisting of phenol red free DMEM/Ham's F12 media supplemented with charcoal stripped FBS (5%), NuSerum (5%), L-glutamine (4 mM), penicillin-streptomycin (1000 U/ml, 100 $\mu$g/ml) and gentimicin (75 $\mu$g/ml), seeded in 100 mm petri dish and incubated at 37° C. in 5%$CO_2$. After 20 minutes, the cells are rinsed with PBS and fresh medium added, this was repeated again at 24 hours. The cells are confluent after approximately 1 week. The endothelial cells are routinely fed twice a week and, when confluent, trypsinized and seeded at a 1:7 ratio. Cell mediated oxidation of 12.5 $\mu$g/mL LDL is allowed to proceed in the presence of the compound to be evaluated (5 $\mu$M) for 4 hours at 37° C. Results are expressed as the percent inhibition of the oxidative process as measured by the TBARS (thiobarbituric acid reactive substances) method for analysis of free aldehydes (Yagi K., Biochem Med 15:212–216 (1976)).

D12 Hypothalmic Cell Test Procedure

D12 rat hypothalamic cells are subcloned from the RCF17 parental cell line and stored frozen. They are routinely grown in DMEM:F12 (1:1), glutaMAX-1 (2 mM), penicillin (100 U/ml)-streptomycin (100 mg/ml), plus 10% fetal bovine serum (FBS). The cells are plated in phenol red-free medium (DMEM:F12, glutaMAX, penicillin-streptomycin) containing 2–10% charcoal stripped FBS at a subconfluent density (1–4×10 6 cells/150 mm dish). The cells are refed 24 h later with medium containing 2% stripped serum. To test for agonist activity, cells are treated with 10 nM 17b-estradiol or various doses of test compound (1 mM or a range from 1 pM to 1 mM). To test for antagonist activity the cells are treated with 0.1 nM 17$\beta$-estradiol in the absence or presence of varying doses (100 pM to 1 mM) of test compound. Control dishes are also treated with DMSO as a negative control. Forty-eight hours after hormone addition, the cells are lysed and binding test procedure performed.

For each binding test procedure 100–150 mg protein is incubated with 10 nM $^3$H-R5020+100-fold excess R5020 in a 150 ml volume. Triplicate reactions (three with R5020, three without R5020) are prepared in a 96 well plate. The protein extract is added first followed by $^3$H-R5020 or $^3$H-R5020+100x unlabeled R5020. The reaction is performed for 1–2 hr at room temperature . The reaction is stopped by the addition of 100 ml cold 5% charcoal (Norit SX4), 0.5% dextran 69K (Pharmacia) in TE pH 7.4. After 5 min at room temperature, the bound and unbound ligand are separated by centrifugation (5 min, 1000 RCF, 4° C.). The supernatant solution (~150 ml) is removed and transferred to a scintillation vial. Following the addition of scintillation fluid (Beckman Ready Protein+), the samples are counted for 1 min in a scintillation counter.

Progesterone Receptor in the CNS Preoptic Area

Sixty (60) day old female Sprague-Dawley rats are ovariectomized. The animals are housed in an animal care facility with a 12-h light, 12-h dark photoperiod and free access to tap water and rodent chow.

Ovariectomized animals are randomly divided into groups that are injected with vehicle (50% DMSO, 40% PBS, 10% ethanol vehicle), 17$\beta$-estradiol (200 ng/kg) or the compound to be tested. Additional animals are injected with the test compound 1 hr prior to injection of 17$\beta$-estradiol to evaluate the antagonistic properties of this compound. Six hrs after s.c. injection, animals are euthanized with a lethal dose of $CO_2$ and their brains collected and frozen.

Tissue collected from animals is cut on a cryostat at −16° C. and collected on Silane-coated microscope slides. The section-mounted slides are then dried on a slide warmer maintained at 42° C. and stored in desiccated slide boxes at −80° C. Prior to processing, the desiccated slide boxes are slowly warmed to room temperature (−20° C. for 12–16 hrs; 4° C. for 2 hrs; room temperature for 1 hr) to eliminate condensation formation on slides and thus minimize tissue and RNA degradation. The dry slides are loaded into metal racks, postfixed in 4% paraformaldehyde (pH 9.0) for 5 min and processed as previously described.

A plasmid containing a 815 bp fragment of the rat PR cDNA 9 (ligand binding domain) is linearized and used to generate a S 35-UTP labeled probe that is complimentary to a portion of the rat PR mRNA. Processed section-mounted slides are hybridized with 200 ml of hybridization mix containing the riboprobe (4–6×10 6 DPM/slide) and 50% formamide and incubated overnight in a 55° C. humidified chamber. In the morning, the slides are placed in metal racks that are immersed in 2×SSC (0.15M NaCl, 0.015M sodium citrate; pH 7.0)/10 mM DTT. The racks are all transferred to a large container and washed in 2×SSC/ 10 mM DTT for 15 min at RT with gentle agitation. Slides are then washed in RNase buffer at 37° C. for 30 min, treated with RNase A (20 mg/ml) for 30 min at 37° C., and washed for 15 min in room temperature 1×SSC. Subsequently, the slides are washed (2×30 min) in 65° C. in 0.1×SSC to remove nonspecific label, rinsed in room temperature 0.1×SSC for 15 min and dehydrated with a graded series of alcohol: ammonium acetate (70%, 95%, and 100%). Air dried slides are opposed to x-ray film for 3 days and then photographically processed. The slides from all animals are hybridized, washed, exposed and photographically processed together to eliminate differences due to interassay variation in conditions.

Rat Hot Flush—CNS Effects

Ovariectomized-female, 60 day-old Sprague-Dawley rats are obtained following surgery. The surgeries are done a minimum of 8 days prior to the first treatment. The animals are housed individually under 12 h light/dark cycle and given standard rat chow and water ad libitum.

Two control groups are included in every study. Doses are prepared based on mg/kg mean group body weight in either 10% DMSO in sesame oil (sc studies) or in 1.0% tween 80 in saline (po studies). Animals are administered test compounds at doses ranging from 0.01 to 10 mg/kg mean group body weight. Vehicle and ethinyl estradiol (EE) controls (0.1 mg/kg, sc or 0.3 mg/kg, po) control groups are included in each test. When the compounds are tested for their antagonist activity, EE is coadministered at 0.1 or 0.3 mg/kg for sc or po studies, respectively. The test compounds are administered up to the day tail skin temperature is measured.

After the acclimation period of four days, the animals are treated once daily with the compound(s) of interest. There are 10 animals/treatment group. Administration of the compound is either by sc injection of 0.1 ml in the nape of the neck or po in a volume of 0.5 ml. On the 3rd day of treatment, a morphine pellet (75 mg morphine sulfate) is implanted subcutaneously. On the 5th day of treatment, one or two additional morphine pellets are implanted. On the eighth day, approximately half of the animals are injected with Ketamine (80 mg/kg, intramuscularly) and a thermocouple, connected with to a MacLab Data Acquisition System (API Insturments, Milford, Mass.) is taped on the tail approximately one inch from the root of the tail. This system allowed the continuous measurement of tail skin temperature. Baseline temperature is measured for 15 min, then naloxone (1.0 mg/kg) is given sc (0.2 ml) to block the effect of morphine and tail skin temperature is measured for one hour thereafter. On the ninth day, the remaining of the animals are set up and analyzed similarly.

Vasomotor Function in Isolated Rat Aortic Rings

Sprage-Dawley rats (240–260 grams) are divided into 4 groups:

1. Normal non-ovariectomized (intact)
2. Ovariectomized (ovex) vehicle treated
3. Ovariectomized 17β-estradiol treated (1 mg/kg/day)
4. Ovariectomized animals treated with test compound (i.e., 1 mg/kg/day)

Animals are ovariectomized approximately 3 weeks prior to treatment. Each animal receives 1 mg/kg/day of either 17-β estradiol sulfate or test compound suspended in distilled, deionized water with 1% tween-80 by gastric gavage. Vehicle treated animals received an appropriate volume of the vehicle used in the drug treated groups.

Animals are euthanized by $CO_2$ inhalation and exsanguination. Their thoracic aortas are rapidly removed and placed in 37° C. physiological solution with the following composition (mM): NaCl (54.7), KCl (5.0), $NaHCO_3$ (25.0), $MgCl_2$ $2H_2O$ (2.5), D-glucose (11.8) and $CaCl_2$ (0.2) gassed with $CO_2$—$O_2$, 95%5% for a final pH of 7.4. The advantitia is removed from the outer surface and the vessel is cut into 2–3 mm wide rings. Rings are suspended in at 10 mL tissue bath with one end attached to the bottom of the bath and the other to a force transducer. A resting tension of 1 gram is placed on the rings. Rings are equilibrated for 1 hour, signals are acquired and analyzed.

After equilibration, the rings are exposed to increasing concentrations of phenylephrine ($10^{-8}$ to $10^{-4}$ M) and the tension recorded. Baths are then rinsed 3 times with fresh buffer. After washout, 200 mM L-NAME is added to the tissue bath and equilibrated for 30 minutes. The phenylephrine concentration response curve is then repeated.

Eight Arm Radial Arm Maze—Cognition Enhancement

Male Sprague-Dawley, CD rats (Charles River, Kingston, N.Y.) weighing 200–250 g on arrival are used. For one week, the rats are housed, six per cage, with standard laboratory chow and water available ad libitum. Housing is in a colony room maintained at 22° C. and had a 12 hour light/dark cycle with lights on at 6:00 AM. Following habituation to the facility, animals are individually housed and maintained at 85% of free-feeding weight. Once stable weights are attained, the rats are acclimated to the 8-arm radial maze.

The structure of the maze is an adaptation from that of Peele and Baron (Pharmacology, Biochemistry, and Behavior, 29:143–150, 1988). The maze is elevated to a height of 75.5 cm and composed of a circular area surrounded by 8 arms radiating away from the center, equidistant from one another. Each arm is 58 cm long×13 cm high. A clear plexiglass cylinder is loared to enclose the animal in the center portion of the maze prior to the start of each session. Each arm of the maze is equipped with 3 sets of photocells interfaced to a data acquisition unit, which in turn is interfaced to a computer. The photocells are used to track the movement of the rat in the maze. Pellet feeders located above food cups at the end of each arm, dispensed two 45 mg chocolate pellets when the outer photocell of the arm is activated for the first time in a given session. The maze is located in a testing room with black and white geometric posters on each wall to serve as visual cues. During all training and testing procedures, white noise is audible (~70 db).

The training procedure consists of five phases, each with daily sessions lasting 5 or 10 minutes. A 10 second delay is imposed between the time the rat is placed in the center portion of the maze and when the cylinder is raised to begin the session. During Phase 1, food-restricted pairs of rats are placed on the maze for 10 minutes with 45 mg chocolate food pellets scattered throughout the 8 arms of the maze. During Phase II, each rat is placed individually on the maze for a 10 minute period, with pellets scattered from the middle photocell to the food cup of each arm. During Phase II, each rat is placed on the maze for a 10 minute period, with food pellets located only in and around the food cups in each arm. In Phase IV, each rat is allowed 10 minutes to collect two pellets from each arm. Re-entry into an arm is considered an error. Rats are trained daily in this manner until they achieved criterion performance with less than or equal to 2 total errors on three consecutive days of training. Total habituation and training time is approximately 3 weeks.

Test compound is prepared in phosphate buffered saline and administered in a volume of 1 ml/kg. Scopolamine HBr (0.3 mg/kg s.c.) served as the impairing agent, producing an increase in error rate (loss of memory). Test compound is given intraperitoneally simultaneously with scopolamine, 30 minutes prior to the first maze exposure on any given test day.

To assess the test compound, an 8×8 balanced latin square for repeated measures is designed, in order to achieve a high experimental efficiency with the least amount of animals. Eight experimental sessions, two per week, are conducted with the 8 treatments (vehicle, scopolamine, 3 doses of test compound in combination with scopolamine) randomized within each session. Each treatment followed every other treatment the same number of times. Therefore, the residual effect of every treatment could be estimated and removed from the direct treatment effect. Following ANOVA, multiple comparisons are performed using Dunnett's two-sided test on adjusted means.

Animals that did not make 4 correct choices within 5 minutes during the first exposure, or that had not made a total of 8 choices by the end of the 2nd exposure, are considered to have "timed-out" for that session. Any animal that "timed-out" following administration of more than one dose of the test compound is excluded from the analysis.

Neuroprotection

Inhibition of Time-Dependent Death of Cells in Primary Cortical Neuron Cultures

Primary cortical neurons were produced from rat brains that were 0–1 day old using a variation of methods described by Monyer et al. 1989, Brain Research 483:347–354. Dispersed brain tissue was grown in DMEM/10% PDHS (pregnant donor horse. serum) for three days and then treated with cytosine arabinoside (ARC) for two days to remove contaminating glial cells. On day 5, the ARC media was removed and replaced with DMEM/10% PDHS. The neuronal cells were cultured for a further 4–7 days before use.

Control primary neuronal cultures show progressive cell death between days 12 and 18 in culture. Twelve cultures were evaluated on days 12 and 16 for levels of the enzyme lactate dehydrogenase (LD) after adding test compound to 6 cultures maintained in DMEM and 10% PDHS on day 9 and maintaining the remaining cultures as controls. LD was assayed using a variation of the method by Wroblewski et al. 1955, Proc. Soc. Exp. Biol. Med. 90:210–213. LD is a cytosolic enzyme which is commonly used in both clinical and basic research to determine tissue viability. An increase in media LD is directly related to cell death.

Neuroprotection Against Cytotoxicity Induced by Hypoglycemia

C6 glioma cells obtained from ATCC were plated in RPMI media with FBS at a concentration of 1×10<6> cells/ml in FALCON 25 cm² tissue culture flasks. Four hours prior to the onset of hypoglycemia, the maintenance media was discarded, monolayers were washed twice in the appropriate media and then incubated for four hours at 37° C. in either serum free or serum free plus test compound. Kreb's Ringer Phosphate buffer was used to wash the monolayers twice before the addition of appropriate glucose treatment. RPMI medium contains 2 mg glucose/ml; flasks were divided into groups of 6 each receiving 100% glucose (2 mg/ml), 80% glucose (1.6 mg/ml), 60% glucose (1.2 mg/ml) or 0% glucose (buffer) or supplemented with test compound. All flasks were incubated for 20 hours and then evaluated for total, live, and dead cell number utilizing trypan blue.

Neuroprotection Against Excitotoxic Amino Acids

Five culture dishes containing SK-N-SH neuroblastoma cells were treated with test compound and 5 culture dishes were treated with RPMI media. Four hours later, all cell were treated with NMDA (500 mu M) for 5 minutes. Total live cells and dead cells were then determined.

Neuroprotection Against Oxygen-Glucose Deprivation

Analysis of pyknotic nuclei to measure apoptosis: Cortical neurons are prepared from E18 rat fetus and plated in 8-well chamber slides precoated with poly-D-lysine (10 ng/ml) and serum at a density of 100,000 cells/well. Cells are plated in high glucose DMEM containing 10% FCS and kept in the incubator at 37° C. with 10% $CO_2$/90% air. On the next day, serum is removed by replacing culture media with high glucose DMEM containing B27 supplement and cells are kept in the incubator without further media change until the day of experiment. On day 6, slides are divided into two groups; control group and OGD group. Cells in control group receive DMEM with glucose and custom B27 (without antioxidants). Cells in OGD group receive no-glucose DMEM with custom B27, which has been degassed under vacuum for 15 min. Cells are flushed with 90% $N_2$/10% $CO_2$ for 10 min in an airtight chamber and incubated at 37° C. for 6 hrs. After 6 hrs, both control and OGD cells are subject to replacement of media containing either vehicle (DMSO) or test compound in glucose-containing DMEM with custom B27. Cells are returned to normoxic incubator at 37° C. After 24 hrs, cells are fixed in 4% PFA for 10 min at 4° C. and stained with Topro (Fluorescent nuclear binding dye). Apoptosis is assessed using Laser Scanning Cytometer by measuring pyknotic nuclei.

Measurement of LDH release as an indication of cell death: Cortical neurons are prepared from E18 rat fetus and plated in 48-well culture plates precoated with poly-D-lysine (10 ng/ml) and serum at a density of 150,000 cells/well. Cells are plated in high glucose DMEM containing 10% FCS and kept in the incubator at 37° C. with 10% $CO_2$/90% air. On the next day, serum is removed by replacing culture media with high glucose DMEM containing B27 supplement. On day 6, cells are divided into two groups; control group and OGD group. Cells in control group receive DMEM with glucose and custom B27 (without antioxidants). Cells in OGD group receive no-glucose DMEM with custom B27, which has been degassed under vacuum for 15 min. Cells are flushed with 90% $N_2$/10% $CO_2$ for 10 min in an airtight chamber and incubated at 37° C. for 6 hrs. After 6 hrs, both control and OGD cells are subject to replacement of media containing either vehicle (DMSO) or test compound in glucose-containing DMEM with custom B27. Cells are returned to normoxic incubator at 37° C. After 24 hrs, cell death is assessed by measuring cellular release of LDH (lactate dehydrogenase) into the culture medium. For LDH assay, an aliquot of 50 µl culture medium is transferred into the 96 well plate. After the addition of 140 µl 0.1M potassium phosphate buffer (pH 7.5) and 100 µl 0.2 mg/ml NADH, the plate is let sit in the dark at room temperature for 20 min. The reaction is initiated by the addition of 10 µl of sodium pyruvate. The plate is read immediately at 340 nM in a Thermomax plate reader (Molecular Devices). The absorbance, an index of NADH concentration, is recorded every 6 seconds for 5 minutes and the slope indicating the rate of NADH disappearance is used to calculate LDH activity.

$$\text{LDH Activity(U/ml)} = (\Delta A/\text{min})(TCF)(20)(0.0833)/(.78)$$

where:
 0.0833=proportionality constant
 0.78=instrument light path length (cm)

HLA Rat Test Procedure—Crohn's Disease and Inflammatory Bowel Disorders

Male HLA-B27 rats are obtained from Taconic and provided unrestricted access to a food (PMI Lab diet 5001) and water. At the start of the study, rats are 22–26 weeks old.

Rats are dosed subcutaneously once per day for seven days with one of the formulations listed below. There are five rats in each group and the last dose is administered two hours before euthanasia.

vehicle (50% DMSO/50% Dulbecco's PBS)
 17α-ethinyl-17β-estradiol (10 µg/kg)
 test compound Stool quality is observed daily and graded according to the following scale: Diarrhea=3; soft stool=2; normal stool=1. At the end of the test procedure, serum is collected and stored at −70° C. A section of colon is prepared for histological analysis and an additional segment is analyzed for myeloperoxidase activity.

The following method is used to measure myeloperoxidase activity. Colon tissue is harvested and flash frozen in liquid nitrogen. A representative sample of the entire colon is used to ensure consistency between samples. The tissue is stored at −80° C. until use. Next, the tissue is weighed (approximately 500 mg) and homogenized in 1:15 w/v of 5 mM $H_2KPO_4$ (pH 6) washing buffer. The tissue is spun down at 20,000×g in a Sorvall RC 5B centrifuge for 45 minutes at 2–8° C. Supernatant is then discarded. Tissue is resuspended and homogenized in 2.5ml (1:5 w/v) of 5OmM $H_2KPO_4$ with 10 mM EDTA and 0.5% Hex Ammonium Bromide to help solubilize the intracellular MPO. Tissue is frozen in liquid Nitrogen, thawed in a 37° C.-water bath and sonicated for 15 seconds to ensure membrane lysis. This procedure is repeated 3 times. Samples are then kept on ice for 20 minutes and centrifuged at 12,000×g for 15 minutes at 2–8° C. The supernatant is analyzed following these steps.

The test mixture is prepared by adding 2.9 ml of 50 mM $H_2KPO_4$ with 0.167 O-Dianisidine/ml with 0.0005% $H_2O_2$ into a reaction tube. When hydrogen peroxide is degraded, O-Dianisidine is oxidized and absorbs at 460 nm in a concentration dependent manner. The mixture is heated to 25° C. One hundred (100) µL of the tissue supernatant is added to the reaction tube, incubated for one minute at 25° C., then 1 ml is transferred to a disposable plastic cuvette. OD is measured every 2 minutes reaction time at 460 nm against a blank containing 2.9 ml of the reaction mixture and 100 µl of the 0.5% ammonium bromide solution.

Enzyme activity units are quantified by comparison of absorbence @ 460 to a standard curve prepared with purified human MPO 31.1 UnitsNial. The MPO is reconstituted and serially diluted using 50 mM $H_2KPO_4$ with 10 mM EDTA and 0.5% Hex Ammonium Bromide to four known concentrations. Sample absorbencies are compared against this curve to determine activity.

Histological analysis is performed as follows. Colonic tissue is immersed in 10% neutral buffered formalin. Each specimen of colon is separated into four samples for evaluation. The formalin-fixed tissues are processed in a vacuum infiltration processor for paraffin embedding. The samples are sectioned at 5 µm and then stained with hematoxylin and eosin (H&E) for blinded histologic evaluations using a scale modified after Boughton-Smith. After the scores are completed the samples are unblinded, and data are tabulated and analyzed by ANOVA linear modeling with multiple mean comparisons.

Based on the results obtained in the standard pharmacological test procedure, the compounds of this invention are estrogen receptor modulators useful in the treatment or inhibition of conditions, disorders, or disease states that are at least partially mediated by an estrogen deficiency or excess, or which may be treated or inhibited through the use of an estrogenic agent. The compounds of this invention are particularly useful in treating a peri-menopausal, menopausal, or postmenopausal patient in which the levels of endogenous estrogens produced are greatly diminished. Menopause is generally defined as the last natural menstrual period and is characterized by the cessation of ovarian function, leading to the substantial diminution of circulating estrogen in the bloodstream. As used herein, menopause also includes conditions of decreased estrogen production that may be surgically, chemically, or be caused by a disease state which leads to premature diminution or cessation of ovarian function.

Accordingly, the compounds of this invention are useful in treating or inhbiting osteoporosis and in the inhibition of bone demineralization, which may result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatment or inhibition for osteoarthritis, hypocalcemia, hypercalcemia, Paget's disease, osteomalacia, osteohalisteresis, multiple myeloma and other forms of cancer having deleterious effects on bone tissues.

The compounds of this invention are also useful in treating or inhibiting benign or malignant abnormal tissue growth, including prostatic hypertrophy, uterine leiomyomas, breast cancer, endometriosis, endometrial cancer, polycystic ovary syndrome, endometrial polyps, benign breast disease, adenomyosis, ovarian cancer, melanoma, prostrate cancer, cancers of the colon, CNS cancers, such as glioma or astioblastomia.

The compounds of this invention are cardioprotective and they are useful in in lowering cholesterol, triglycerides, Lp(a), and LDL levels; inhibiting or treating hypercholesteremia; hyperlipidemia; cardiovascular disease; atherosclerosis; peripheral vascular disease; restenosis, and vasospasm; and inhibiting vascular wall damage from cellular events leading toward immune mediated vascular damage. These cardiovascular protective properties are of great importance when treating postmenopausal patients with estrogens to inhibit osteoporosis and in the male when estrogen therapy is indicated.

The compounds of this invention are also antioxidants, and are therefore useful in treating or inhibiting free radical induced disease states. Specific situations in which antioxidant therapy is indicated to be warranted are with cancers, central nervous system disorders, Alzheimer's disease, bone disease, aging, inflammatory disorders, peripheral vascular disease, rheumatoid arthritis, autoimmune diseases, respiratory distress, emphysema, prevention of reperfusion injury, viral hepatitis, chronic active hepatitis, tuberculosis, psoriasis, systemic lupus erythematosus, adult respiratory distress syndrome, central nervous system trauma and stroke.

The compounds of this invention are also useful in providing cognition enhancement, and in treating or inhibiting senile dementias, Alzheimer's disease, cognitive decline, neurodegenerative disorders, providing neuroprotection or cognition enhancement.

The compounds of this invention are also useful in treating or inhibiting inflammatory bowel disease, ulcerative proctitis, Crohn's disease, and colitis; menopausal related conditions, such as vasomotor symptoms including hot flushes, vaginal or vulvar atrophy, atrophic vaginitis, vaginal dryness, pruritus, dyspareunia, dysuria, frequent urination, urinary incontinence, urinary tract infections, vasomotor symptoms, including hot flushes, myalgia, arthralgia, insomnia, irritability, and the like; male pattern baldness; skin atrophy; acne; type II diabetes; dysfunctional uterine bleeding; and infertility.

The compounds of this invention are useful in disease states where amenorrhea is advantageous, such as leukemia, endometrial ablations, chronic renal or hepatic disease or coagulation diseases or disorders.

The compounds of this invention can be used as a contraceptive agent, particularly when combined with a progestin.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. Effective administration of the compounds of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The preparation of representative examples of this invention is described below.

Preparation of Compounds in Schemes 1
2-(2,4-Dimethoxy-phenyl)-1-(2,4,6-trimethoxy-phenyl)-ethanone 6

A solution of 2,4-dimethoxyphenyl acetic acid (7.9 g, 38 mmol) in $CH_2Cl_2$ (50 mL) plus a few drops of DMF was treated with $SOCl_2$ (5.0 mL, 76 mmol) and the reaction was allowed to stir for 3 h at rt. The reaction mixture was then concentrated and taken up in a small amount of dichloroethane and added dropwise, at 0° C., to a solution of 1,3,5-trimethoxybenzene (12.8 g, 76 mmol) and $AlCl_3$ (7.3 g, 57 mmol) in 50 mL dichloroethane. After 20 minutes at 0° C., the reaction was carefully quenched with 2 N HCl aq. The organic layer was separated, dried over $MgSO_4$, filtered and concentrated to give a dark oil which was chromatographed on $SiO_2$ (3:7 EtOAc/hexanes to 1:1 EtOAc/hexanes) to yield the desired product as a white solid (6.2 g): Mp 109–111° C.; $^1$H NMR (CDCl$_3$) δ 7.06 (d, 1H, J=8.1 Hz), 6.41 (dd, 1H, J=8.1Hz, 2.4Hz), 6.39 (d, 1H, J=2.4Hz), 6.04 (s, 2H), 3.97 (s, 2H), 3.80 (s, 3H), 3.78 (s, 3H), 3.74 (s, 6H), 3.71 (s, 3H); MS FI 347 (M+H)$^+$.

2-(2,4-Dimethoxy-phenyl)-1-(2-hydroxy-4,6-dimethoxy-phenyl)-ethanone 7

A solution of compound 6 (3.2 g, 9.3 mmol) and $AlCl_3$ (1.4 g, 10.2 mmol) in dichloroethane (30 mL) was heated to 60° C. for 15 minutes and additional $AlCl_3$ (1.3 g) was added followed by an additional 15 minutes of heating at 60° C. The reaction was cooled and poured into 2 N HCl aq. The layers were separated and the organic phase was dried and concentrated to give a solid which was triturated with MeOH to give a white solid (2.1 g): Mp 116–119° C.; $^1$H NMR (CDCl$_3$) δ 13.9 (s, 1H), 7.00 (d, 1H, J=8.0 Hz), 6.50–6.45 (m, 2H), 6.08 (d, 1H, J=2.4 Hz), 5.95 (d, 1H, J=2.4 Hz), 4.24 (s, 2H), 3.87 (s, 3H), 3.83 (s, 3H), 3.81 (s, 3H) 3.76 (s, 3H); MS FI 333 (M+H)$^+$.

3-(2,4-Dimethoxy-phenyl)-5,7-dimethoxy-chromen-4-one 8

A solution of 7 (3.2 g, 9.6 mmol) in triethylorthoformate (40 mL) and morpholine (10 mL) was heated to 120° C. for 4 hr. The reaction was allowed to cool to rt, poured into 2 N HCl and extracted with $CH_2Cl_2$. The $CH_2Cl_2$ was dried over $MgSO_4$, concentrated and chromatographed on $SiO_2$ (2:98 $MeOH/CH_2Cl_2$ to 4:96 ($MeOH/CH_2Cl_2$)) to give a the product 8 (1.5 g): Mp 202–204° C.; $^1$H NMR (CDCl3) δ 7.73 (s, 1H), 7.23 (d, 1H, J=9.0 Hz), 6.54–6.51 (m, 2H), 6.44 (d, 1H, J=2.3 Hz), 6.36 (d, 1H, J=2.3 Hz), 3.91 (s, 3H), 3.89 (s, 3H), 3.83 (s, 3H), 3.75 (s, 3H); MS FI 343 (M+H)$^+$.

3-(2,4-Dihydroxy-Dhenyl)-5-hydroxy-7-methoxy-chromen-4-one 9

A solution of 8 (1.4 g, 4.1 mmol) in $CH_2Cl_2$ (50 mL) was treated with a dropwise addition of $BBr_3$ (16 mL, 1 M in $CH_2Cl_2$, 16 mmol) and the reaction allowed to stir for 1 h at rt. The reaction was then quenched by the slow addition of MeOH and concentrated to give a solid. The solid was washed with 10% $NaHCO_3$ and then dissolved in EtOAc/MeOH, evaporated onto silica gel and chromatographed (EtOAC:hexanes, 1:1) to yield a yellow solid which was triturated with EtOAc and filtered to give 9 as a light yellow solid (1.05 g): Mp 246–248; $^1$H NMR (DMSO-$d_6$) δ 13.0 (s, 1H), 9.40 (s, 1H), 9.33 (s, 1H), 8.24 (s, 1H), 6.98 (d, 1H, J=8.2 Hz), 6.65 (d, 1H, J=2.2 Hz), 6.41 (d, 1H, J=2.2 Hz), 6.37 (d, 1H, J=2.3Hz), 6.27 (dd, 1H, J=8.2, 2.3 Hz), 3.87 (s, 3H); MS FI(Neg) 399 (M−H)$^-$.

2.6-Dihvdroxy-8-methoxy-10,11-dioxa-benzo[b]fluoren-5-one 10

A solution of 9 (0.68 g, 2.3 mmol) in THF (50 mL) was treated with DDQ (o.77g, 3.4 mmol) and heated at 55° C. for 5 h. The reaction was cooled and the THF evaporated off. The resulting oil was partitioned between EtOAc and 10% sodium sulfite aq. The organic layer was dried over $MgSO_4$ and concentrated and chromatographed on silica gel (EtOAc/hexanes; 3:7) to give a white solid which was triturated with MeOH and filtered to give the product as a white solid (0.22 g): Mp 265–268° C.; $^1$H NMR (DMSO-$d_6$) δ 12.94 (s, 1H), 10.00 (s, 1H), 7.74 (d, 1H, J=8.4 Hz), 7.13 (d, 1H, J=2.0 Hz), 6.94 (dd, 1H, J=8.4 Hz, 2.1 Hz), 6.87 (d, 1H, J=2.3 Hz), 6.51 (d, 1H, J=2.2 Hz), 3.34 (s, 3H); MS FI (neg) 297 (M−H)$^-$.

2,6,8-Trihydroxy-10,11-dioxa-benzo[b]fluoren-5-one 4 (Lupinalbin A)

A mixture consisting of 10 (0.17 g) and 7g Pyr-HCl was heated to 190° C. for 45 min. The reaction was allowed to cool and then partitioned between water and EtOAc. The EtOAc was dried over $MgSO_4$, filtered, concentrated and chromatographed on silica gel (EtOAc/hexanes; 3:7) to give the product as a white solid (0.07 g): Mp 318–322 (dec); $^1$H NMR (DMSO-$d_6$) δ 12.90 (s, 1H), 10.97 (br s, 1H), 9.99 (br s, 1H), 7.72 (d, 1H, J=8.4 Hz), 7.11 (d, 1H, J=2.1 Hz), 6.93 (dd, 1H, J=8.4 Hz, 2.1 Hz), 6.56 (d, 1H, J=2.1 Hz), 6.30 (d, 1H, J=2.1 Hz); MS FI (neg) 283 (M−H)$^-$.

Preparation of Compounds in Scheme 2

3-Dimethylamino-1-(2-hydroxy-4-methoxy-phenyl)-propenone 12

A solution of 2-Hydroxy, 4-methoxy acetophenone 11 (4.5 g, 27 mmol) and DMF diethoxy acetal (6.5 g, 54 mmol) in toluene was heated to reflux for 3 h. The reaction was cooled and concentrated to give a solid which was triturated with MeOH to yield 12 as a yellow solid (4.0 g): Mp 144–147° C.

3-Bromo-7-methoxy-chromen-4-one 13

Compound 12 (4.0 g, 18.1 mmol) in $CH_2Cl_2$ (50 mL) was treated with dropwise addition of $Br_2$ (2.9 g, 18.1 mmol). After stirring for 10 min at rt, the $CH_2Cl_2$ was washed with a 10% $Na_2SO_3$ aq., dried over $MgSO_4$ and concentrated to give a yellow solid which was triturated to yield compound 13 (2.7 g) as a white solid.

3-(2,4-Dimethoxy-phenyl)-7-methoxy-chromen-4-one 14

A solution of 13 (4.0 g, 15.8 mmol) and 2,4-dimethoxy benzeneboronic acid (3.4 g, 19.0 mmol) and $Pd(Ph_3)_4$ (0.79 g) in toluene/EtOH (50 mL/5 mL) and 2M $Na_2CO_3$ aq. (30 mL) was heated to reflux. After 5 h, the reaction was cooled and the organic layer dried over $MgSO_4$, concentrated and chromatographed on silica gel (EtOAc/hexanes 3:7 to EtOAc/hexanes 1:1) to yield 14 as a solid which was triturated with MeOH to give a tan solid.

3-(2,4-Dihydroxy-phenyl)-7-hvdroxy-chromen-4-one 15

At 0° C., a solution of 14 (1.0 g, 3.2 mmol) in $CH_2Cl_2$ was treated with $BBr_3$ (16 mL, 16 mmol, 1 M in $CH_2Cl_2$) and the reaction mixture was allowed to stir at rt for 18 h. The reaction was quenched slowly with MeOH, concentrated and taken up in EtOAc. The EtOAc layer was washed with 2N HCl aq. And the EtOAc was dried over $MgSO_4$, filtered, concentrated and chromatographed on silica gel (EtOAC/hexanes; 1:1) to yield 15 as a white solid (0.5 g).

2,8-Dihydroxy-10,11-dioxa-benzo[b]fluoren-5-one 16

A mixture of 15 (0.25 g, 0.93 mmol) and DDQ (0.42 g, 1.87 mmol) in dioxane was heated to 90° C. for 45 min. The reaction was allowed to cool and poured into 10% Na2SO3 and extracted with EtOAc. The EtOAc was dried over $MgSO_4$, filtered and concentrated to give a yellow solid that was triturated with MeOH to give 16 as a white solid (0.050 g): Mp>300° C.; $^1$H NMR (DMSO $d_6$) δ 10.88 (br s, 1H), 9.93 (br s, 1H), 8.05 (d, 1H, J=8.6 Hz), 7.77 (d, 1H, J=8.4 Hz), 7.10 (d, 1H, J=1.9 Hz), 7.05 (d, 1H, J=2.0 Hz), 7.01 (dd, 1H, J=8.6 Hz, 2.1 Hz), 6.92 (dd, 1H, J=8.4 Hz, 1.9 Hz); MS FI (neg) 267 (M−H)$^-$.

What is claimed is:

1. A compound of formula I, having the structure

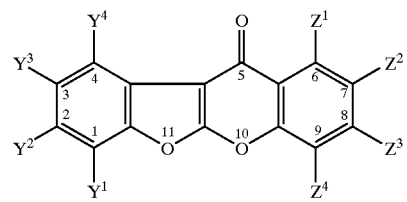

wherein $Y^1, Y^2, Y^3, Y^4, Z^1, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO$_2$, or —$COR^3$;

R is hydrogen, alkyl of 1–6 carbon atoms, —$CF_3$, benzyl, —$CO_2R^1$, or —$COR^3$;

$R^1$ is —$CF_3$, alkyl of 1–6 carbon atoms, or benzyl;

$R^2$ is hydrogen or alkyl of 1–6 carbon atoms;

$R^3$ is alkyl of 1–6 carbon atoms, phenyl, thienyl, furyl, —$NR^4R^5$, or —$CF_3$;

$R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1, Y^2, Y^3, Y^4, Z^1, Z^2, Z^3$, and $Z^4$ is —OR; and at least one of $Y^1, Y^2, Y^3, Y^4, Z^1, Z^2, Z^3$, and $Z^4$ is not hydrogen or —OR.

2. The compound according to claim 1, wherein $Y^1, Y^4, Z^1, Z^2, Z^3$, and $Z^4$ are hydrogen, or —OR; with at least one of $Y^1, Y^4 Z^1, Z^2, Z^3$, and $Z^4$ not being —OR.

3. The compound according to claim 2, wherein R is hydrogen or alkyl of 1–6 carbon atoms.

4. A compound which is 2,6-dihydroxy-8-methoxy-10,11-dioxa-benzo[b]fluoren-5-one or a pharmaceutically acceptable salt thereof.

5. A compound which is 2,8-dihydroxy-10,11-dioxa-benzo[b]fluoren-5-one or a pharmaceutically acceptable salt thereof.

6. A method of treating or inhibiting osteoporosis or inhibiting bone demineralization in a mammal in need thereof, which comprises providing to said mammal an effective amount of a compound of formula I, having the structure

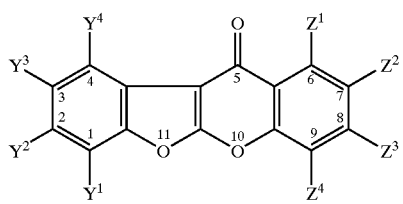

wherein $Y^1, Y^2, Y^3, Y^4, Z^1, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO$_2$, or —$COR^3$;

R is hydrogen, alkyl of 1–6 carbon atoms, —$CF_3$, benzyl, —$CO_2R^1$, or —$COR^3$;

$R^1$ is —$CF_3$, alkyl of 1–6 carbon atoms, or benzyl;

$R^2$ is hydrogen or alkyl of 1–6 carbon atoms;

$R^3$ is alkyl of 1–6 carbon atoms, phenyl, thienyl, furyl, —$NR^4R^5$, or —$CF_3$;

$R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1, Y^2, Y^3, Y^4, Z^1, Z^2, Z^3$, and $Z^4$ is —OR.

7. A method of treating or inhibiting inflammatory bowel disease, Crohn's disease, ulcerative proctitis, or colitis in a mammal in need thereof, which comprises providing to said mammal an effective amount of a compound of formula I, having the structure

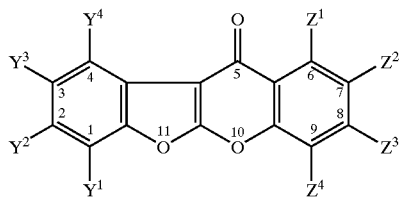

wherein $Y^1, Y^2, Y^3, Y^4, Z^1, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO$_2$, or —$COR^3$;

R is hydrogen, alkyl of 1–6 carbon atoms, —$CF_3$, benzyl, —$CO_2R^1$, or —$COR^3$;

$R^1$ is —$CF_3$, alkyl of 1–6 carbon atoms, or benzyl;

$R^2$ is hydrogen or alkyl of 1–6 carbon atoms;

$R^3$ is alkyl of 1–6 carbon atoms, phenyl, thienyl, furyl, —$NR^4R^5$, or —$CF_3$;

$R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1, Y^2, Y^3, Y^4, Z^1, Z^2, Z^3$, and $Z^4$ is —OR.

8. A method of treating or inhibiting prostatic hypertrophy, uterine leiomyomas, breast cancer, endometriosis, endometrial cancer, polycystic ovary syndrome, endometrial polyps, benign breast disease, adenomyosis, ovarian cancer, melanoma, prostrate cancer, colon cancer, glioma or astioblastomia in a mammal in need thereof, which comprises providing to said mammal an effective amount of a compound of formula I, having the structure

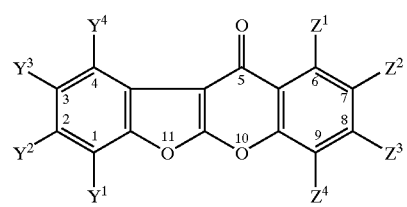

wherein $Y^1, Y^2, Y^3, Y^4, Z^1, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO$_2$, or —$COR^3$;

R is hydrogen, alkyl of 1–6 carbon atoms, —$CF_3$, benzyl, —$CO_2R^1$, or —$COR^3$;

$R^1$ is —$CF_3$, alkyl of 1–6 carbon atoms, or benzyl;

$R^2$ is hydrogen or alkyl of 1–6 carbon atoms;

$R^3$ is alkyl of 1–6 carbon atoms, phenyl, thienyl, furyl, —$NR^4R^5$, or —$CF_3$;

$R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1, Y^2, Y^3, Y^4, Z^1, Z^2, Z^3$, and $Z^4$ is —OR.

9. A method of lowering cholesterol, triglycerides, Lp(a), or LDL levels; inhibiting or treating hypercholesteremia; hyperlipidemia; cardiovascular disease; atherosclerosis; peripheral vascular disease; restenosis, or vasospasm; or inhibiting vascular wall damage from cellular events leading toward immune mediated vascular damage in a mammal in need thereof, which comprises providing to said mammal an effective amount of a compound of formula I, having the structure

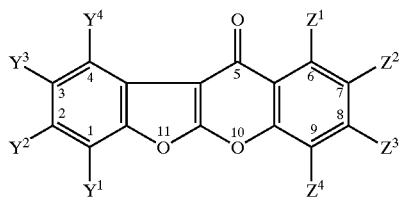

wherein
- $Y^1, Y^2, Y^3, Y^4, zI, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO$_2$, or —$COR^3$;
- R is hydrogen, alkyl of 1–6 carbon atoms, —$CF_3$, benzyl, —$CO_2R^1$, or —$COR^3$;
- $R^1$ is —$CF_3$, alkyl of 1–6 carbon atoms, or benzyl;
- $R^2$ is hydrogen or alkyl of 1–6 carbon atoms;
- $R^3$ is alkyl of 1–6 carbon atoms, phenyl, thienyl, furyl, —$NR^4R^5$, or —$CF_3$;
- $R^4$ and $R^5$ are each, independently, hydrogen, alkyl of 1–6 carbon atoms, or are taken together to form a 5–7 memebered saturated heterocyclic ring containing a nitrogen and 4–6 carbon atoms;
- or a pharmaceutically acceptable salt thereof, with the proviso that at least one of $Y^1, Y^2, Y^3, Y^4, Z^1, Z^2, Z^3$, and $Z^4$ is —OR.

10. A method of treating or inhibiting providing cognition enhancement or neuroprotection; or treating or inhibiting senile dementias, Alzheimer's disease, cognitive decline, or neurodegenerative disorders in a mammal in need thereof, which comprises providing to said mammal an effective amount of a compound of formula I, having the structure

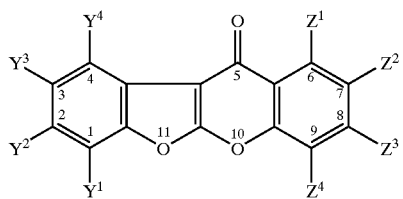

wherein
- $Y^1, Y^2, Y^3, Y^4, Z^1, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO$_2$, or —$COR^3$;
- R is hydrogen, alkyl of 1–6 carbon atoms, —$CF_3$, benzyl, —$CO_2R^1$, or —$COR^3$;
- $R^1$ is —$CF_3$, alkyl of 1–6 carbon atoms, or benzyl;
- $R^2$ is hydrogen or alkyl of 1–6 carbon atoms;
- $R^3$ is alkyl of 1–6 carbon atoms, phenyl, thienyl, furyl, —$NR^4R^5$, or —$CF_3$;
- $R^4$ and $R^5$ are each, independently, hydrogen, alkyl of 1–6 carbon atoms, or are taken together to form a 5–7 memebered saturated heterocyclic ring containing a nitrogen and 4–6 carbon atoms;
- or a pharmaceutically acceptable salt thereof, with the proviso that at least one of $Y^1, Y^2, Y^3, Y^4, Z^1, Z^2, Z^3$, and $Z^4$ is —OR.

11. A method of treating or inhibiting free radical induced disease states in a mammal in need thereof, which comprises providing to said mammal an effective amount of a compound of formula I, having the structure

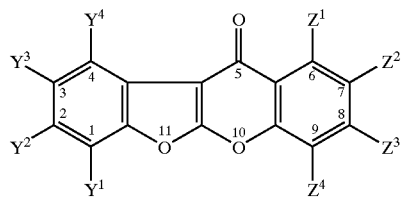

wherein
- $Y^1, Y^2, Y^3, Y4, Z^1, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO$_2$, or —$COR^3$;
- R is hydrogen, alkyl of 1–6 carbon atoms, —$CF_3$, benzyl, —$CO_2R^1$, or —$COR^3$;
- $R^1$ is —$CF_3$, alkyl of 1–6 carbon atoms, or benzyl;
- $R^2$ is hydrogen or alkyl of 1–6 carbon atoms;
- $R^3$ is alkyl of 1–6 carbon atoms, phenyl, thienyl, furyl, —$NR^4R^5$, or —$CF_3$;
- $R^4$ and $R^5$ are each, independently, hydrogen, alkyl of 1–6 carbon atoms, or are taken together to form a 5–7 memebered saturated heterocyclic ring containing a nitrogen and 4–6 carbon atoms;
- or a pharmaceutically acceptable salt thereof, with the proviso that at least one of $Y^1, Y^2, Y^3, Y^4, Z^1, Z^2, Z^3$, and $Z^4$ is —OR.

12. A method of treating or inhibiting vaginal or vulvar atrophy; atrophic vaginitis; vaginal dryness; pruritus; dyspareunia; dysuria; frequent urination; urinary incontinence; urinary tract infections in a mammal in need thereof, which comprises providing to said mammal an effective amount of a compound of formula I, having the structure

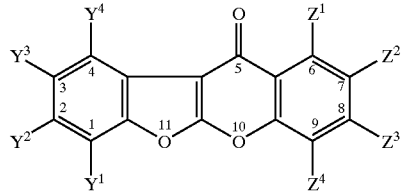

wherein
- $Y^1, Y^2, Y^3, Y^4, Z^1, Z^2, Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN; —$NO_2$, —$CH_2NO_2$, —$CH_2CH_2NO_2$, —CH=CHNO$_2$, or —$COR^3$;
- R is hydrogen, alkyl of 1–6 carbon atoms, —$CF_3$, benzyl, —$CO_2R^1$, or —$COR^3$;
- $R^1$ is —$CF_3$, alkyl of 1–6 carbon atoms, or benzyl;
- $R^2$ is hydrogen or alkyl of 1–6 carbon atoms;
- $R^3$ is alkyl of 1–6 carbon atoms, phenyl, thienyl, furyl, —$NR^4R^5$, or —$CF_3$;
- $R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1$, $Y^2$, $Y^3$, $Y^4$, $Z^1$, $Z^2$, $Z^3$, and $Z^4$ is —OR.

13. A method of treating or inhibiting vasomotor symptoms in a mammal in need thereof, which comprises providing to said mammal an effective amount of a compound of formula I, having the structure

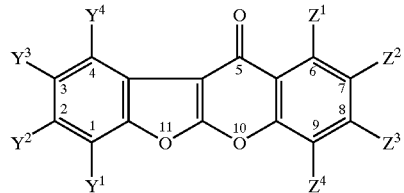

wherein $Y^1$, $Y^2$, $Y^3$, $Y^4$, $Z^1$, $Z^2$ $Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO_2, or —$COR^3$;

R is hydrogen, alkyl of 1–6 carbon atoms, —$CF_3$, benzyl, —$CO_2R^1$, or —$COR^3$;

$R^1$ is —$CF_3$, alkyl of 1–6 carbon atoms, or benzyl;

$R^2$ is hydrogen or alkyl of 1–6 carbon atoms;

$R^3$ is alkyl of 1–6 carbon atoms, phenyl, thienyl, furyl, —$NR^4R^5$, or —$CF_3$;

$R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1$, $Y^2$, $Y^3$, $Y^4$, $Z^1$, $Z^2$, $Z^3$, and $Z^4$ is —OR.

14. A method of treating or inhibiting menopausal or postmenopausal disorders in a mammal in need thereof, which comprises providing to said mammal an effective amount of a compound of formula I, having the structure

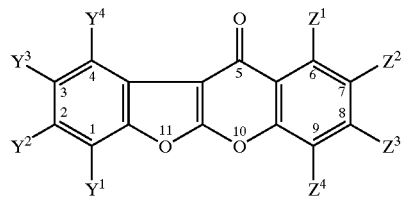

wherein $Y^1$, $Y^2$, $Y^3$, $Y^4$, $Z^1$, $Z^2$, $Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO_2, or —$COR^3$;

R is hydrogen, alkyl of 1–6 carbon atoms, —$CF_3$, benzyl, —$CO_2R^1$, or —$COR^3$;

$R^1$ is —$CF_3$, alkyl of 1–6 carbon atoms, or benzyl;

$R^2$ is hydrogen or alkyl of 1–6 carbon atoms;

$R^3$ is alkyl of 1–6 carbon atoms, phenyl, thienyl, furyl, —$NR^4R^5$, or —$CF_3$;

$R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1$, $Y^2$, $Y^3$, $Y^4$, $Z^1$, $Z^2$, $Z^3$, and $Z^4$ is —OR.

15. A pharmaceutical composition which comprises a compound of formula I, having the structure

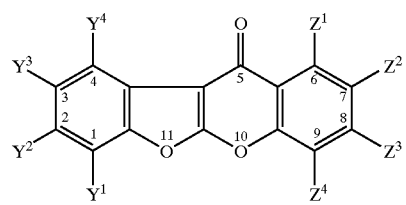

wherein $Y^1$, $Y^2$, $Y^3$, $Y^4$, $Z^1$, $Z^2$, $Z^3$, and $Z^4$ are each, independently, hydrogen, —OR, halogen, —$CF_3$, —$CF_2CF_3$, —$CH_2CF_3$, —$SR^2$, —CN, —$CH_2CN$, —$CH_2CH_2CN$, —CH=CHCN, —$NO_2$, —$CH_2NO_2$, —$CH_2CH_2NO_2$, —CH=CHNO_2, or —$COR^3$;

R is hydrogen, alkyl of 1–6 carbon atoms, —$CF_3$, benzyl, —$CO_2R^1$, or —$COR^3$;

$R^1$ is —$CF_3$, alkyl of 1–6 carbon atoms, or benzyl;

$R^2$ is hydrogen or alkyl of 1–6 carbon atoms;

$R^3$ is alkyl of 1–6 carbon atoms, phenyl, thienyl, furyl, —$NR^4R^5$, or —$CF_3$;

$R^4$ and $R^5$ are each, independently, hydrogen, alkyl of 1–6 carbon atoms, or are taken together to form a 5–7 memebered saturated heterocyclic ring containing a nitrogen and 4–6 carbon atoms;

or a pharmaceutically acceptable salt thereof, with the proviso that at least one of $Y^1$, $Y^2$, $Y^3$, $Y^4$, $Z^1$, $Z^2$, $Z^3$, and $Z^4$ is —OR, and a pharmaceutical carrier.

* * * * *